US012599479B2

(12) United States Patent
Lim et al.

(10) Patent No.: US 12,599,479 B2
(45) Date of Patent: *Apr. 14, 2026

(54) HEART VALVE COMPRISING A CROWN PIECE INTERCONNECTED TO LEAFLETS, A TOP CUFF AND A BOTTOM CUFF; AND A MEDICAL IMPLANT

(71) Applicant: VENUS MEDTECH (HANGZHOU), INC., Hangzhou (CN)

(72) Inventors: Hou-Sen Lim, Hangzhou (CN); Wolfgang Gotz, Regensberg (DE)

(73) Assignee: VENUS MEDTECH (HANGZHOU), INC., Hangzhou (CN)

( * ) Notice: Subject to any disclaimer, the term of this patent is extended or adjusted under 35 U.S.C. 154(b) by 1350 days.

This patent is subject to a terminal disclaimer.

(21) Appl. No.: 16/888,776

(22) Filed: May 31, 2020

(65) Prior Publication Data

US 2020/0289258 A1     Sep. 17, 2020

Related U.S. Application Data

(63) Continuation of application No. 15/126,066, filed on Sep. 14, 2016, now abandoned.

(51) Int. Cl.
*A61F 2/24*          (2006.01)
(52) U.S. Cl.
CPC .......... *A61F 2/2412* (2013.01); *A61F 2/2418* (2013.01); *A61F 2/2439* (2013.01); *A61F 2220/0075* (2013.01); *A61F 2250/006* (2013.01)

(58) Field of Classification Search
CPC ........ A61F 2/24; A61F 2/2418; A61F 2/2412; A61F 2220/0075; A61F 2250/006; B23P 11/00
See application file for complete search history.

(56) References Cited

U.S. PATENT DOCUMENTS

| | | | | |
|---|---|---|---|---|
| 3,657,744 A | * | 4/1972 | Ersek | A61B 17/11 623/902 |
| 3,777,591 A | | 12/1973 | Thomasian | |
| 4,624,822 A | * | 11/1986 | Arru | A61F 2/24 8/94.11 |
| 5,600,874 A | | 2/1997 | Jungkind | |
| 6,033,412 A | | 3/2000 | Losken et al. | |
| 6,302,891 B1 | | 10/2001 | Nadal | |

(Continued)

FOREIGN PATENT DOCUMENTS

| | | |
|---|---|---|
| CA | 2412063 A1 | 5/2004 |
| CN | 101151003 A | 3/2008 |

(Continued)

*Primary Examiner* — Leslie A Lopez
(74) *Attorney, Agent, or Firm* — Raymond Sun

(57) ABSTRACT

Heart valve comprising a crown piece interconnected to leaflets, a top cuff and a bottom cuff; and a medical implant. The present invention relates to a heart valve (100), comprising at least two leaflets (101, 101', 101"); at least one crown piece (111) interconnected to the leaflets (101, 101', 101") and intended to be interconnected to a frame (1) of a medical implant or a heart valve assembly; a top cuff (121); and a bottom cuff (131), the crown piece (111), the top cuff (121) and the bottom cuff (131) each being ring-shaped, and each of the top cuff (121) and the bottom cuff (131) being interconnected with the crown piece (111).

16 Claims, 5 Drawing Sheets

(56) References Cited

U.S. PATENT DOCUMENTS

| | | | |
|---|---|---|---|
| 7,510,575 B2* | 3/2009 | Spenser ................. A61F 2/2427 | |
| | | | 623/2.18 |
| 7,662,122 B2 | 2/2010 | Sterling | |
| 7,824,443 B2 | 11/2010 | Salahieh et al. | |
| 7,938,851 B2 | 5/2011 | Olson et al. | |
| 8,366,760 B2 | 2/2013 | Kumoyama | |
| 8,381,362 B2 | 2/2013 | Hammerslag et al. | |
| 8,468,657 B2 | 6/2013 | Soderberg et al. | |
| 8,500,789 B2 | 8/2013 | Wuebbeling et al. | |
| 8,516,662 B2 | 8/2013 | Goodman et al. | |
| 2001/0049555 A1 | 12/2001 | Gabbay | |
| 2003/0125805 A1 | 7/2003 | Johnson et al. | |
| 2005/0081339 A1 | 4/2005 | Sakabayashi | |
| 2005/0085851 A1 | 4/2005 | Fiehler et al. | |
| 2006/0156517 A1 | 7/2006 | Hammerslag et al. | |
| 2006/0173524 A1 | 8/2006 | Salahieh et al. | |
| 2006/0178740 A1* | 8/2006 | Stacchino ............. A61F 2/2436 | |
| | | | 623/2.18 |
| 2006/0259124 A1 | 11/2006 | Matsuoka et al. | |
| 2006/0265055 A1 | 11/2006 | Lauterjung | |
| 2006/0282150 A1 | 12/2006 | Olson et al. | |
| 2006/0287717 A1 | 12/2006 | Rowe et al. | |
| 2007/0088421 A1 | 4/2007 | Loewen | |
| 2007/0168014 A1 | 7/2007 | Jimenez et al. | |
| 2008/0071311 A1 | 3/2008 | White et al. | |
| 2009/0005863 A1 | 1/2009 | Goetz et al. | |
| 2010/0004606 A1 | 1/2010 | Hansen et al. | |
| 2010/0076541 A1 | 3/2010 | Kumoyama | |
| 2010/0174290 A1 | 7/2010 | Wiiebbeling et al. | |
| 2010/0185277 A1* | 7/2010 | Braido ...................... A61F 2/89 | |
| | | | 623/2.37 |
| 2010/0234883 A1 | 9/2010 | White et al. | |
| 2011/0040366 A1 | 2/2011 | Goetz et al. | |
| 2011/0172702 A1 | 7/2011 | Fiehler et al. | |
| 2011/0191992 A1 | 8/2011 | Chen | |
| 2011/0266384 A1 | 11/2011 | Goodman et al. | |
| 2012/0022635 A1 | 1/2012 | Yamashita | |
| 2012/0059448 A1 | 3/2012 | Parker et al. | |
| 2012/0109280 A1 | 5/2012 | McHugo | |
| 2012/0296418 A1 | 11/2012 | Bonyuet et al. | |
| 2012/0330401 A1 | 12/2012 | Sugimoto et al. | |
| 2013/0035759 A1 | 2/2013 | Gross et al. | |
| 2013/0096664 A1* | 4/2013 | Goetz ................... A61F 2/2418 | |
| | | | 623/1.26 |
| 2013/0239303 A1 | 9/2013 | Cotterman et al. | |
| 2013/0317598 A1 | 11/2013 | Rowe et al. | |
| 2014/0277417 A1 | 9/2014 | Schraut et al. | |
| 2016/0100939 A1* | 4/2016 | Armstrong ............ A61F 2/2418 | |
| | | | 623/2.12 |

FOREIGN PATENT DOCUMENTS

| | | |
|---|---|---|
| CN | 101180010 A | 5/2008 |
| EP | 2382947 A1 | 11/2011 |
| GB | 2491479 A | 12/2012 |
| WO | WO00/72909 A1 | 12/2000 |
| WO | WO2008/029296 A2 | 3/2008 |
| WO | WO2009/109348 A1 | 9/2009 |
| WO | WO2009/149215 A1 | 12/2009 |
| WO | WO2011/063972 A1 | 6/2011 |
| WO | WO2011/101128 A1 | 8/2011 |
| WO | WO2011/109813 A2 | 9/2011 |
| WO | WO2012/084178 A2 | 6/2012 |
| WO | WO2012/177942 A2 | 12/2012 |
| WO | WO2013/028387 A2 | 2/2013 |
| WO | WO2013/059743 A1 | 4/2013 |
| WO | WO2013/075215 A1 | 5/2013 |
| WO | WO2013/114214 A2 | 8/2013 |
| WO | WO2015/014960 A1 | 2/2015 |

* cited by examiner

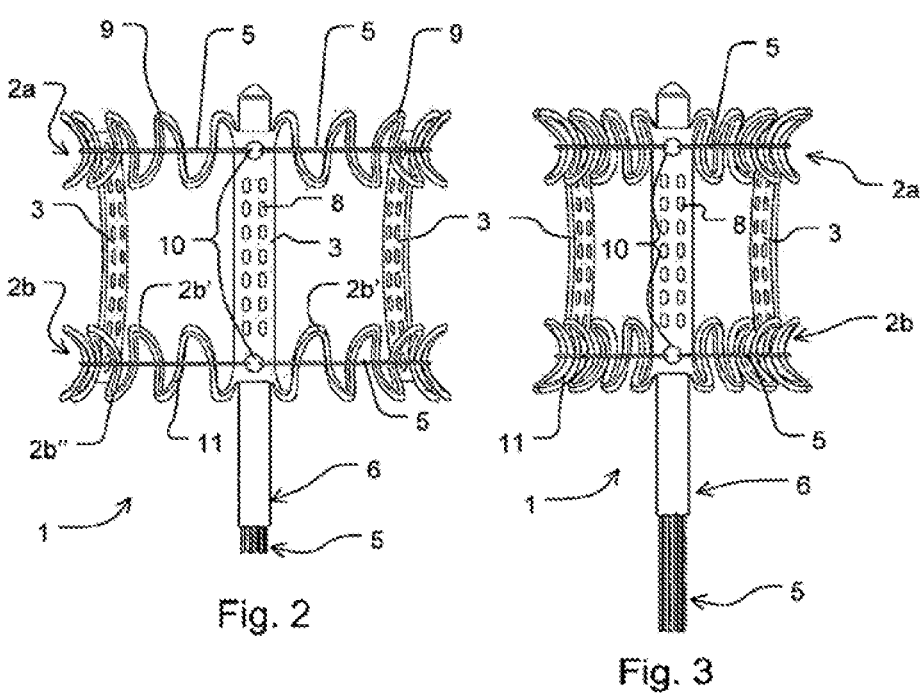
Fig. 2
Fig. 3
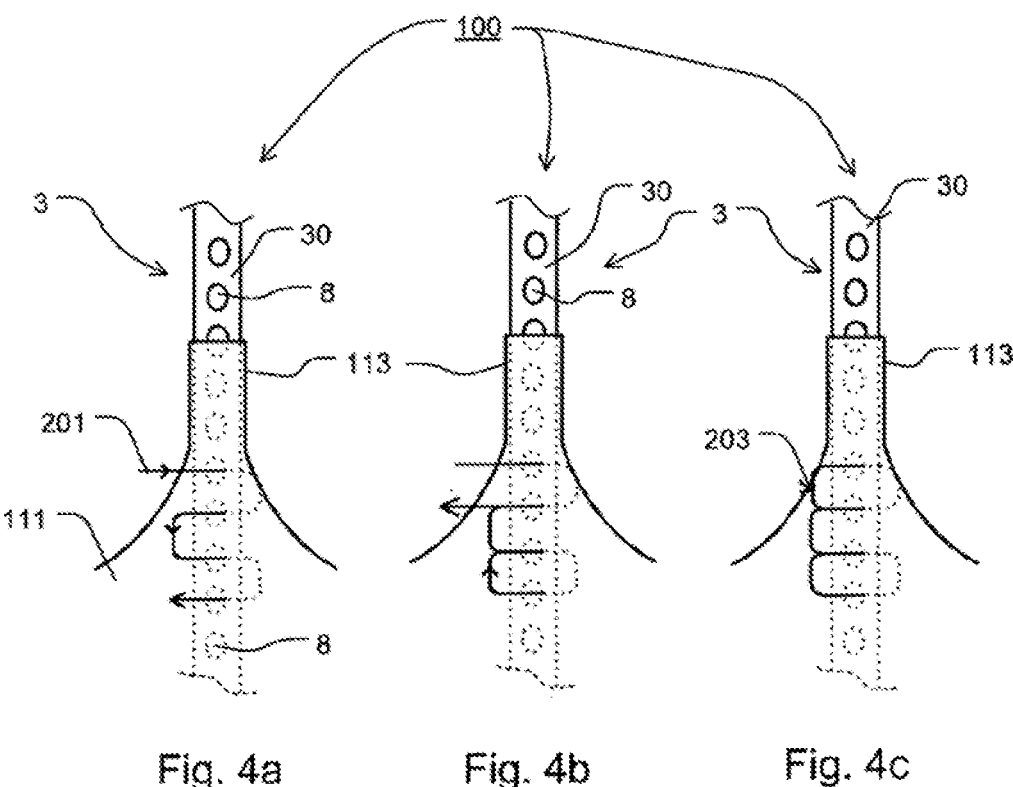
Fig. 4a    Fig. 4b    Fig. 4c

Fig. 5a                  Fig. 5b

HEART VALVE COMPRISING A CROWN PIECE INTERCONNECTED TO LEAFLETS, A TOP CUFF AND A BOTTOM CUFF; AND A MEDICAL IMPLANT

The present invention relates to a heart valve according to claim 1 and to a medical implant (short hereinafter: implant) according to claim 7.

From WO 2009/109348 A1, implants comprising a frame and a heart valve attached to the frame are known.

One object of the present invention is to provide another heart valve and another medical implant comprising such a heart valve.

This object may be solved by a heart valve having the features of claim 1. Insofar as the terms "invention" and/or "embodiment" are used in the following, and/or features are presented as being optional, this should be interpreted in such a way that the only protection sought is that of the invention as claimed.

According to the present invention, a heart valve is suggested which comprises at least two heart valve leaflets. It also comprises at least one crown piece (also referred to as 'triangle' hereinafter) interconnected to the leaflets. The crown piece is preferably intended to be interconnected, directly or indirectly, for example sewed, to a frame (also referred to as the support or the body of the implant or a stent by way of example hereinafter).

The heart valve further comprises a top cuff and a bottom cuff.

The crown piece, the top cuff and the bottom cuff are each rings or ring-shaped, and both the top cuff and the bottom cuff are interconnected with the crown piece.

Also, according to the present invention, a medical implant comprising a heart valve according to the present invention is suggested. The implant has a frame or support or stent that is foldable and/or unfoldable.

The frame comprises at least or exactly one first guiding structure for guiding or comprising at least one tension thread for folding and/or unfolding the frame around or along the frame, for example at an outside or an circumference thereof.

The frame comprises at least or exactly one second guiding structure different from the first guiding structure also for guiding or comprising at least one tension thread for folding and/or unfolding the implant around or along the frame, for example at an outside or an circumference thereof.

The frame further comprises at least two, preferably three, posts. The posts are arranged between the first and the second guiding structure such that they interconnect the first and the second guiding structure with each other and/or maintain the distance between them.

In the following, the use of the expression "may be" or "may have", and so on, is to be understood synonymously with "in exemplary embodiments is" or "in exemplary embodiments has", respectively, and so on, and is intended to illustrate exemplary embodiments according to the present invention.

Exemplary embodiments according to the present invention are each also subject of dependent claims.

Exemplary embodiments according to the present invention may comprise one or more of the features named hereinafter.

In certain exemplary embodiments according to the present invention, the implant may be folded or unfolded upon implantation by using one or several tension threads or filaments wound around the implant.

In particular exemplary embodiments according to the present invention, the crown piece is foldable and unfoldable.

In certain exemplary embodiments according to the present invention, the crown piece does not comprise a threading, particular exemplary embodiments according to the present invention, the frame of the heart valve does not comprise threading either.

In particular exemplary embodiments according to the present invention, a foldable and/or unfoldable frame or support or stent is a structure that can unfold from a crimped state to an unfolded state, for example because of its, optionally provided, shape memory material.

In some exemplary embodiments according to the present invention, altering the shape of the implant means reducing or increasing a diameter, particularly an external diameter, of the implant. Such an alteration may or may not involve an alteration of the implant's length or any other kind of alteration.

In certain exemplary embodiments according to the present invention, folding the implant means reducing the diameter of the implant. Folding also covers "re-folding" of an once expanded implant.

In some exemplary embodiments according to the present invention, unfolding should be understood as increasing the diameter of the implant, or as expanding.

In certain exemplary embodiments according to the present invention, the diameter of the implant is arranged in a plane perpendicular to a main flow direction of the implant in case fluids flow through the implant after its implantation.

In some exemplary embodiments according to the present invention, at least one of the top cuff and the bottom cuff is formed from a stripe (or strap) or comprises a stripe (or strap, e.g. a thin band that is longer than broad). The stripe is (in its flat state) curved along its length, preferably or at least in a plane of its width.

In certain exemplary embodiments according to the present invention, the top cuff has a width that is smaller than a width of the bottom cuff.

In certain exemplary embodiments according to the present invention, the 'width' refers to an average width of the stripe.

In some exemplary embodiments according to the present invention, the top cuff and the bottom cuff are equally long (or almost equally long).

In particular exemplary embodiments according to the present invention, the top cuff is arranged closer to the leaflets than the bottom cuff.

In some exemplary embodiments according to the present invention, all leaflets are sewed to the crown piece by means of one or exactly one suture or stitch.

In particular exemplary embodiments according to the present invention, a suture is a filament or a thread or yarn. In these embodiments, One suture' means one filament (or thread or yarn) used for sewing two pieces together. In these embodiments, no second filament is used and, in consequence, only one knot is required.

In some exemplary embodiments according to the present invention, both the top cuff and the bottom cuff are sewed to the crown piece by means of one or exactly one suture.

In particular exemplary embodiments according to the present invention, the crown piece is sewed to the posts, preferably using (or via or through) through holes or eyelets of the posts, preferably through at least three or four, preferably consecutive through holes, preferably by means of tabs being small extensions of the crown piece or by leaving out the tabs, preferably by means of one or exactly one suture per post.

In some exemplary embodiments according to the present invention, the suture for interconnecting the crown piece to one post was started from an outer side of that post to an inner side of the post. Preferably, the single knot that interconnects both ends of the suture is arranged on an outside of the post.

In particular exemplary embodiments according to the present invention, the posts are arranged inside a circle or an area circumscribed by the crown piece.

In some exemplary embodiments according to the present invention, the posts are arranged outside the circle or the area circumscribed by at least one of the top cuff and the bottom cuff.

In particular exemplary embodiments according to the present invention, at least one of the first and the second guiding structure comprises or consists of bars (can be struts instead) that are interconnected to each other so as to form a zig-zag pattern or an undulating or meandering pattern. Neighbouring or adjacent or contacting bars are provided for moving relative to each other or for changing a distance or an angle between them (or between sections thereof, respectively) upon folding or unfolding of the implant or frame. The bars are preferably arranged outside the circle or the area circumscribed by at least one of the top cuff and the bottom cuff. In preferred embodiments according to the present invention the bars are covered on their inner side (being the side towards the inner space of the frame or implant) at least in part (s) by at least one of the top cuff and the bottom cuff.

In some exemplary embodiments according to the present invention, the leaflets have a first tab and a second tab arranged at opposite ends of the respective leaflet. The tabs are sewed onto the post of the frame.

In certain exemplary embodiments according to the present invention, the tabs extend from the body of the leaflet.

In particular exemplary embodiments according to the present invention, tabs of two adjacent leaflets are sewed to one post in an overlapping manner.

In certain exemplary embodiments according to the present invention, the tab of a first leaflet is or was sewed onto a post first, and wherein the tab of a second leaflet was sewed onto both the tab of a first leaflet and the post the tab of the first leaflet had been sewed to, all in one running stitch or with one suture.

In some exemplary embodiments according to the present invention, the medical implant comprises exactly three posts.

In certain exemplary embodiments according to the present invention, the heart valve comprises exactly three leaflets. In particular exemplary embodiments according to the present invention, the implant is a heart or cardiac valve assembly.

In certain exemplary embodiments according to the present invention, the crown piece may have up to three sections that are triangle in shape (at least once the crown piece's free ends are put together such that the crown piece forms a ring).

In particular exemplary embodiments according to the present invention, the frame (or support or body) of the implant is made of or comprises a metal or a shape memory material, such as, for example, Nitinol.

In certain exemplary embodiments according to the present invention, the top cuff and the bottom cuff are originally separate pieces, directly or indirectly interconnected with each other by sewing.

In some exemplary embodiments according to the present invention, the crown piece may have sections ending in a tip of a triangle section of the crown piece or in a tab extending from the tip of the triangle, the tab having a free end (before being fixed to, for example, the leaflets).

In certain exemplary embodiments according to the present invention, the crown piece is interposed between the top cuff and the bottom cuff.

In certain exemplary embodiments according to the present invention, at least one of the top cuff and the bottom cuff is made from porcine pericardium or is a fabric.

In some exemplary embodiments according to the present invention, the leaflets are interconnected with, preferably glued or sewed to, the crown piece.

In some exemplary embodiments of the apparatus according to the present invention, the at least one tension thread is a thread. The thread may be a surgical suture thread or similar to it. The thread may have the shape of a rope, a filament or a cord. The thread may be designed as a chain having a plurality of engaging chain links.

In this specification, the term thread or tension thread may also define a plurality of threads or tension threads whenever a person skilled in the art recognizes the exchangeability of the terms.

In certain exemplary embodiments according to the present invention, the implant or its frame is permeable for fluids in its implanted state in its longitudinal direction. "Permeable" means that the fluid may flow through the implant, for example, through an inner lumen thereof.

In particular exemplary embodiments according to the present invention, the frame has features as described in WO 2011/063972 A1 or WO 2009/109348 A1 with respect to the implant.

In certain exemplary embodiments according to the present invention, the implant is configured to have or has tension applied to it by using at least one tension thread. The tension is preferably controlled by altering a length of the pulling device by which it extends out of the interior of the shaft or a catheter or sections thereof.

In some exemplary embodiments according to the present invention, at least one of the heart valve and the frame comprises exclusively, i.e. only, (one or more) materials that are MRI (short for: magnetic resonance imaging) compatible.

In certain exemplary embodiments according to the present invention, at least one of the heart valve and the frame comprises exclusively (one or more) materials that are not magnetic, ferromagnetic, or both.

In some exemplary embodiments according to the present invention, at least one of the heart valve and the frame does not comprise metal or any metal alloy.

In certain embodiments according to the present invention, eat least one of the posts has at least two openings through which tension threads are guided from an inside or inner space of the implant to an outside of the implant and back from the outside to the inside. The tension threads are guided to the outside through a first opening of a first one of the posts and back to the inside—or vice versa—through any second first opening of any second post, the first opening being different from the second opening, and the first post being different from the second post.

In particular exemplary embodiments according to the present invention, the crown piece is interconnected to the frame of a medical implant or a heart valve assembly.

In certain exemplary embodiments according to the present invention, both the top cuff and the bottom cuff are interconnected to bars of a guiding structure of the frame, preferably by sewing, preferably in direct contact to the bars.

Some or all advantages achievable by the heart valve according to the present invention may in certain exemplary embodiments of the present invention also be achieved by medical implant according to the present invention.

Some or all exemplary embodiments according to the present invention may provide for one, several or all of the advantages named above and/or hereafter.

According to the present invention, the top cuff and the bottom cuff may have different widths. If the top cuff and the bottom cuff is now everted to the outside face of the bars both at an upper end and an lower end of the bars by an equal distance (the equal distance is usually equal since it takes the same amount of material or overlap to secure the cuffs on the tips of both the upper parts and the lower parts of the bars), a suture interconnecting the two cuffs (plus the crown piece) will not be positioned in a middle line of the bars. That way, the suture will not be damaged by the bars in a folded state of the implant in which the middle of the bars will usually have to face the highest pressure. At the same token, the suture does not contribute to applying pressure on the leaflets starting about the height of the bars of the guiding structure as the suture will not contribute to narrowing the space about the middle line of the bars due to its position beyond the middle line.

Further, sewing parts by just one suture may contribute in avoiding knots which in turn require space and are prone to damaging neighboring structures such as leaflets.

If, as in particular embodiments according to the present invention, the inner side of the top cuff is interconnected to the outer side of the bottom cuff, the resulting geometrical shape will show a profile that extends with a middle portion thereof into the inner space it circumscribes. In a front cut the geometrical shape may be called concave. That shape may fit best to the also concave shape of the bent bars and the resulting concave shape of the guiding structure which is another advantage.

Providing at least one of the heart valve and the implant to be MRI compatible allows advantageously for controlling the location and orientation of the apparatus or the implant, or both, by MRI upon use of the apparatus or implantation of the implant. No heat, sparks or artefacts are generated during MRI because of the materials chosen for the apparatus or the implant.

In the following, examples of the present invention will be described with reference to the accompanying figures wherein similar or identical assemblies or elements are denoted by same reference numerals.

FIG. 2 shows a medical implant according to the present invention in an expanded state which is expandable and can be reduced in its diameter by use of a means;

FIG. 3 shows the medical implant of FIG. 2 in a non- or less expanded state;

FIGS. 4a-4c show how the heart valve of FIGS. 1a to 1e is being fixed or secured to a frame according to FIG. 2 or 3;

FIGS. 5a-5c show how tabs of adjacent leaflets of the heart valve according one embodiment of the present invention are commonly attached to one post of the frame;

FIG. 1a through FIG. 1e show parts of a heart valve 100 according to a first exemplary embodiment of the present invention.

Figures 1A, 1B, 1C, 1D, 1E:
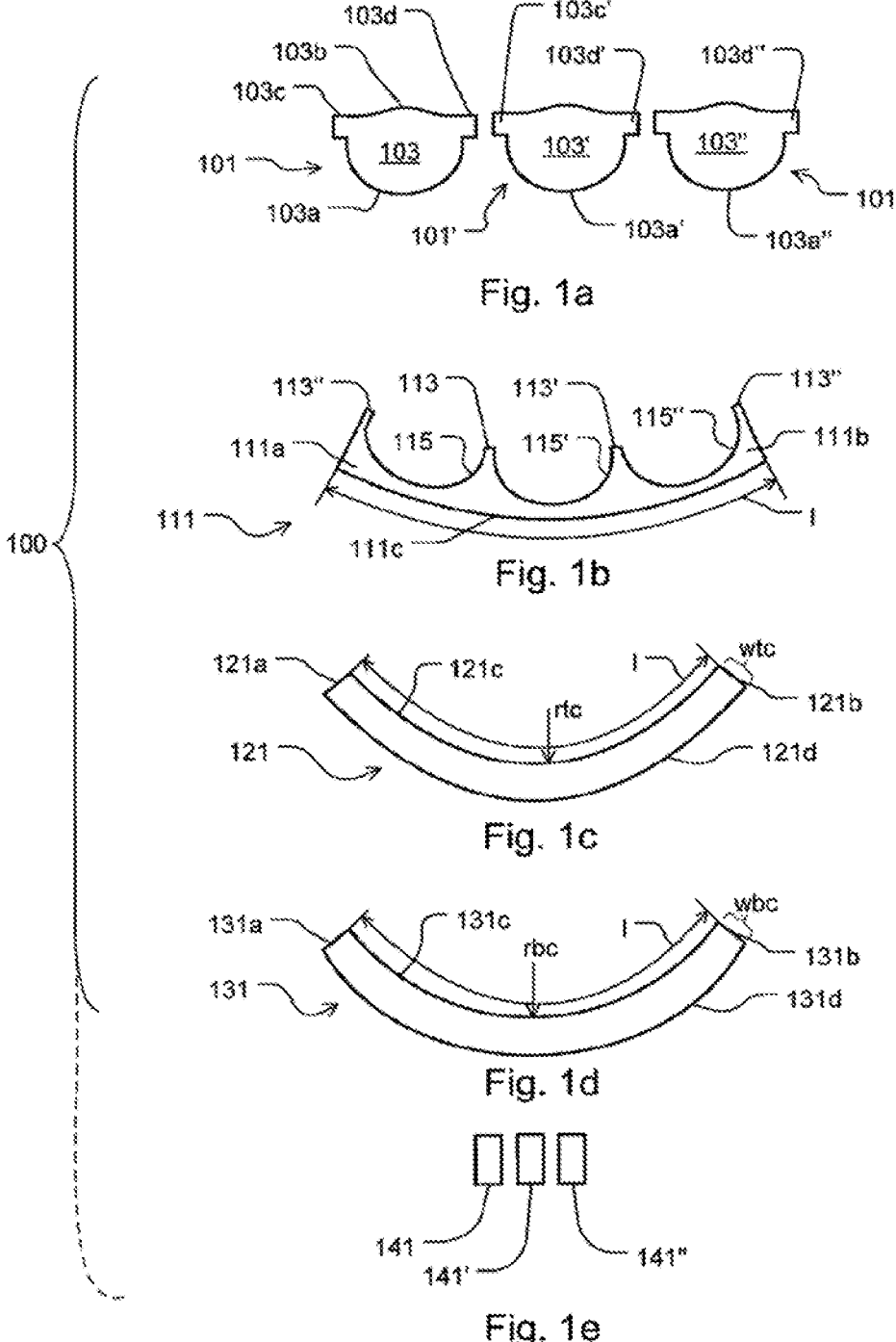
FIG. 1a shows three leaflets of a heart valve according to a first exemplary embodiment of the present invention.
FIG. 1b shows a crown piece of a heart valve according to the first exemplary embodiment of the present invention.
FIG. 1c shows a top cuff of a heart valve according to the first exemplary embodiment of the present invention.
FIG. 1d shows a bottom cuff of a heart valve according to the first exemplary embodiment of the present invention.
FIG. 1e shows three pledges of a heart valve according to the first exemplary embodiment of the present invention.

FIG. 1a shows three leaflets 101, 101' and 101" of the heart valve 100 of the first exemplary embodiment of the present invention. Instead of three leaflets 101, 101' and 101" the heart valve 100 according to the present invention may comprise any other number of leaflets, for example two. In the exemplary embodiment of FIG. 1a, all leaflets 101, 101' and 101" are identical. In other embodiments according to the present invention, at least two of them may, however, be different from each other.

In the exemplary embodiment of FIG. 1a, each leaflet 101, 101', 101" has a body 103, 103', 103", respectively, having a round or curved bottom section 103a, 103a', 103' and a rim section 103b, 103b', 103b" opposing the corresponding curved section 103a, 103a' or 103a". The rim section 103b, 103b', 103b" extends into opposing tabs 103c, 103c', 103" and 103d, 103d', 103d" which form the outmost portions to the opposing sides of the respective body 103, 103' or 103" (i. e. left and to the right of in the illustration of FIG. 1a).

FIG. 1b shows a crown piece 111 of the heart valve 100. In use, the crown piece 111 is formed to a ring by connecting together the free ends 111a and 111b of the stripe shown in FIG. 1b with each other.

The crown piece 111 optionally comprises small tabs 113, 113', 113" and round portions 115, 115' 115". The tabs 113, 113', 113" may be arranged between neighboring round portions 115, 115' 115", respectively, or each.

The round portions 115, 115' 115" are shaped such that their curved rims correspond to the curved sections 103a, 103a' or 103a" of the leaflets 101, 101', 101".

In FIG. 1b, the reference number 113" is used twice. In practice, both small (half-) tabs 113" will contact each other so as to form one single small tab afterwards.

In certain embodiments according to the present invention, the leaflets 101, 101' and 101" and/or the crown piece 111 (and, if applicable, also the pledges (also referred to a pledgets, these terms being, hence, synonyms) 141, 141', 141", see FIG. 1e) are cut (e. g. laser cut) from a (e. g. jib-fixed) bovine pericardium having a preferred thickness between 0.35 and 0.55 mm.

In some embodiments according to the present invention, the leaflets 101, 101' and 101" are all of identical or similar stiffness.

FIG. 1c shows a top cuff 121 of the heart valve 100. As can be seen from FIG. 1c, the top cuff 121, which is used in a ring-shaped form after having united the top cuffs ends 121a and 121b with each other, is formed from a flat stripe. The same applies to a bottom cuff 131 discussed below with reference to FIG. 1d showing a bottom cuff 131 with ends 131a, 131b of the heart valve 100 according to the first exemplary embodiment of the present invention.

The width of the top cuff 121 is denoted with wtc. The width of the bottom cuff 131 is denoted with wbc. In certain embodiments according to the present invention, wtc is smaller than wbc.

The length of the top cuff 121 is denoted with 1. The length of the bottom cuff 131 is denoted with 1 as well since in the exemplary embodiment shown in the figures the top cuff 121 and the bottom cuff 131 are of the same length, at least with respect to a first side 121*c* of the top cuff 121 and a second side 131*c* of the bottom cuff 131. "1" also denotes the length of the lower rim or side 111*c* of crown piece 111. All lengths denoted with 1 are identical in certain embodiments according to the present invention.

The reference numerals rtc and rbc of FIGS. 1*c* and 1*d* denote the radius of the curvature of the top cuff 121 and the bottom cuff 131, respectively. The radius rtc and the radius rbc indicate that the stripes shown in FIGS. 1*c* and 1*d* are not straight but bent within the drawing plane of FIGS. 1*c* and 1*d*. rtc and rbc may be identical, without being limited hereto.

The inner side of top cuff 121 is denoted with 121*c*, the outer side with 121*d*.

The inner side of bottom cuff 131 is denoted with 131*c*, the outer side with 131*d*.

Because of the radius of top cuff 121 and bottom cuff 131, their inner sides 121*c*, 131*c* are shorter than their outer sides 121*d*, 131*d*, respectively.

In particular embodiments according to the present invention, the inner side 121*c* of top cuff 121 is interconnected with the outer side 131*d* of bottom cuff 131. This way, the resulting structure will be generally cylindrical with a middle (or about middle) portion that protrudes into the inner space formed by the resulting structure.

In certain embodiments according to the present invention, top cuff 121 and the bottom cuff 131 are cut (e. g. laser cut) from a (e. g. surface-tension) porcine pericardium having a preferred thickness between 0.15 and 0.25 mm.

The small tabs 113, 113', 113" may be used for a temporary stitch for temporarily securing the crown piece 111 to the frame 1. Both the provided temporary stitch and the small tabs 113, 113', 113" may be cut off and disposed later on.

FIG. 1*e* shows three pledges 141, 141' and 141" of the heart valve 100 according to the first exemplary embodiment of the present invention. The pledges 141, 141' and 141" are optional. The benefit of the potential pledges 141, 141' and 141" are discussed with regards to FIGS. 6*a* to 6*c*. The number of the pledges may correspond to the number of posts 3.

The medical implant according to some embodiments of the present invention comprises a heart valve 100, for example the one discussed with reference to FIGS. 1*a* to 1*d* or 1*e* and a frame 1 or supporting structure, for example the one discussed with reference to FIGS. 2 and 3. In certain embodiments according to the present invention, the medical implant consists of the heart valve 100 and the frame 1.

FIG. 2 shows a frame 1 of an exemplary implant according to the present invention. The frame 1 is expandable and can be reduced again in its diameter. The diameter refers to a plane perpendicular to a longitudinal axis of the frame 1. The longitudinal direction also corresponds to the direction of the extension of the catheter 6 shown in FIG. 2.

Frame 1 comprises at least a first or upper—preferably circular—guiding structure or ring 2*a* and a second or lower—preferably also circular—guiding structure 2*b*. The guiding structures 2*a*, 2*b* are connected to rods or posts 3. In some embodiments, the guiding structures 2*a*, 2*b* can—additionally or alternatively or exclusively—fulfill the function of guiding structures for reins 5. The reins 5 form part of a catheter 6 and serve for applying force or tension or stress, respectively, to the guiding structures 2*a*, 2*b* for the purpose of expanding or folding the frame 1 in a targeted manner. In the example of FIG. 2, the guiding structures 2*a*, 2*b* are each designed having the shape of an outwardly half-open channel through which the reins 5 are guided. The half-open channel is opened in a direction away from the centre of the frame 1. However, the channel can also be shaped to be open to the implant or to any other direction.

In the example of FIG. 2, the guiding structures 2*a*, 2*b* are interrupted by posts 3, i.e. the posts 3 are integrated into the guiding structures 2*a*, 2*b* such that they form sections of the guiding structures 2*a*, 2*b*.

In the embodiment of the frame 1 according to the invention shown in FIG. 2, the posts 3 and/or the guiding structures 2*a*, 2*b* have (round or differently shaped, e. g., oval, rectangular, elliptic, and so on) passage means or apertures 10. In the embodiment shown in FIG. 2, they serve as a passage for the reins 5. The posts 3 also have through openings 8, for example eyelets, which can be arranged in two parallel rows as in FIG. 2, in one row as in FIGS. 4*a* to 4*c*, or in any other arrangement.

Furthermore, the frame 1 can also comprise a number of guiding means 2*a*, 2*b* other than two, for example, one, three, four or more guiding means.

The guiding structures 2*a*, 2*b* can be arranged circularly, however, they can also be arranged non-circularly.

The guiding structures 2*a*, 2*b* can be formed integrally with the implant; however, they can also be fabricated separately.

The guiding structures 2*a*, 2*b* can have the shape of a wave or undulation, respectively; however, they can also be fabricated in any other form, in particular, a non-wavy or non-undulating form.

Independent of all other features, frame 1 or parts thereof can be fabricated from flat material, e. g., a material which has been cut with a laser, wherein, e. g., after having designed a pattern in the flat material, the material is reformed into a tube (optionally by connecting, such as welding, longitudinal sides of the former flat material lane or web, respectively). However, frame 1 can also be fabricated from a tubular material directly.

The guiding structures 2*a*, 2*b* of frame 1 comprise or consist of a plurality of bars 11 which are each connected to another by means of connecting sections 9. The plurality of bars 11 may be arranged in a zig-zag pattern or an undulating or meandering pattern as is exemplary shown in FIG. 2.

FIG. 3 shows the frame 1 of FIG. 2. Two reins 5 have been led or guided around the frame 1 and return back to the catheter 6 through the respectively same passage means or apertures 10. The reins 5 apply a tension or stress on the frame 1, and, in consequence, frame 1 is not completely expanded or unfolded. Rather, the diameter of the frame 1 has been reduced or is being hindered from expanding in a free manner.

At least one of the top cuff 121 and the bottom cuff 131 can be secured to the bars 11 of the second or lower guiding structure 2*b*, for example by using a whip stitch, with, e. g. four stitches per bar 11, preferably evenly spaced. At some or all of the top portions of bars 11, indicated by 2*b'* in FIG. 2 and FIG. 3, and/or at some of all of the bottom portions of the bars 11, indicated by 2*b"* in FIG. 2 and FIG. 3, the curved bottom sections 103*a*, 103*a'*, 103*a"* of the leaflets 101, 101', 101" are additionally secured to the frame 1, for example once again by means of one or more surgeon's knots. Care should be taken to secured the body 103*a*, 103*a'*, 103*a"* only at its rim or seam section.

FIGS. 4*a*-4*c* show how the heart valve 100 of FIGS. 1*a* to 1*d* or 1*e* is being fixed or secured to an exemplary post 3 of a frame 1 according to FIG. 2 or 3 in temporal subsequence.

As can be seen in FIG. 4a, a suture 201 is pierced through the crown piece 111 and then let through a through hole 8 of the post 3. In doing so, the suture is guided from the outside of the heart valve 100 to the inside of the heart valve 100, leaving a suture tail of at least 2 cm on the outside of the heart valve 100. This tail will later be used to make a knot. Next, a running stitch is created down the post 3 going in and out of the through holes 8 (eyelets) until the suture has been guided through four (preferably neighbouring) through holes 8. The suture is then returned back up the post 3 in and out of the through holes 8 until the through hole 8 below the suture tail is reached, see FIG. 4b. The suture is tied off using the starting suture tail using a surgeon's knot 203 or any other knot or fixture. The knot 203 should be on the outside of the heart valve 100 and/or on an outer side 3o of the post 3 as in FIG. 4c.

Figure 5C:
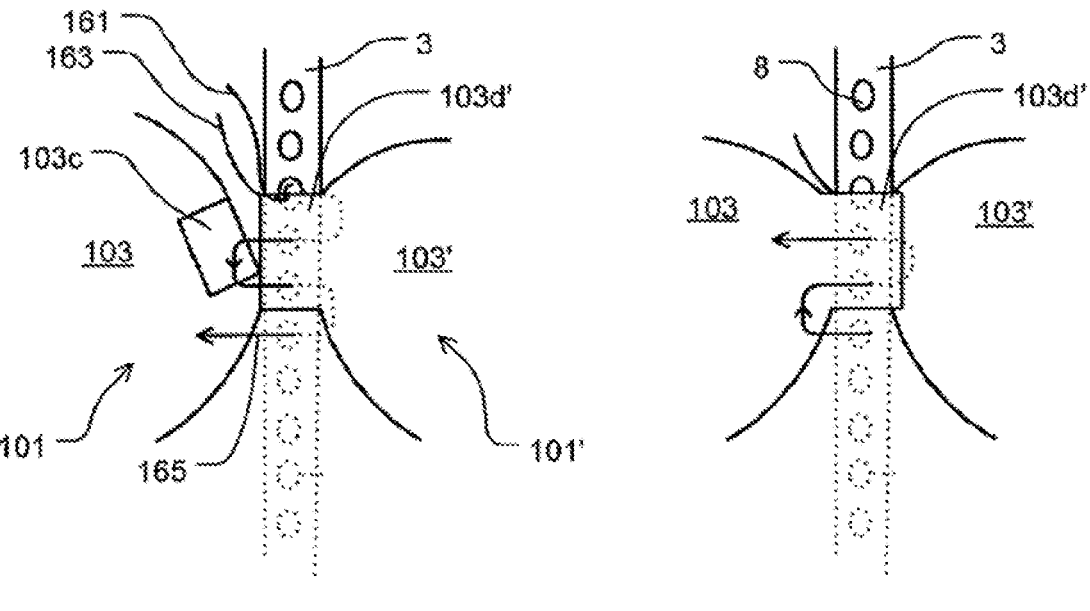
Figure 5C:
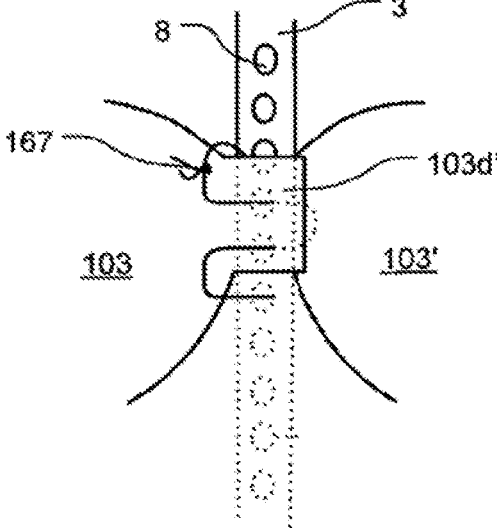

FIGS. 5a to 5c show how a tab 103c and a tab 103d' of adjacent leaflets 101 and 101' are attached to a common post 3 of the frame 1.

As can be seen from FIG. 5a, tab 103c of leaflet 101 is folded over onto the body 103 of leaflet 101, and a knot 161 is created at the top of tab 103d'. Knot 161 secures the heart valve 100 in place on the frame 1. A suture tail 163 of the suture is not cut. With a running stitch 165 going in and out of preferably each eyelet 8 downwards on the tab 103d' which is placed on an outside of the post 3 the tab 103d' is secured more and more to the post 3 until the bottom of tab 103d' is reached.

Now, as is shown in FIG. 5b, tab 103c is folded back over tab 103d' (and hence also on an outside of post 3 although not in contact with the post 3) and the stitch 165 is continued back up the tabs 103c and 103d', again while going in and out of the eyelets 8 until the top of the tabs is reached.

Tail 163 is used for tying off using a suitable knot such as a surgeon's knot 167, see FIG. 5c.

Figures 6A, 6B, 6C:
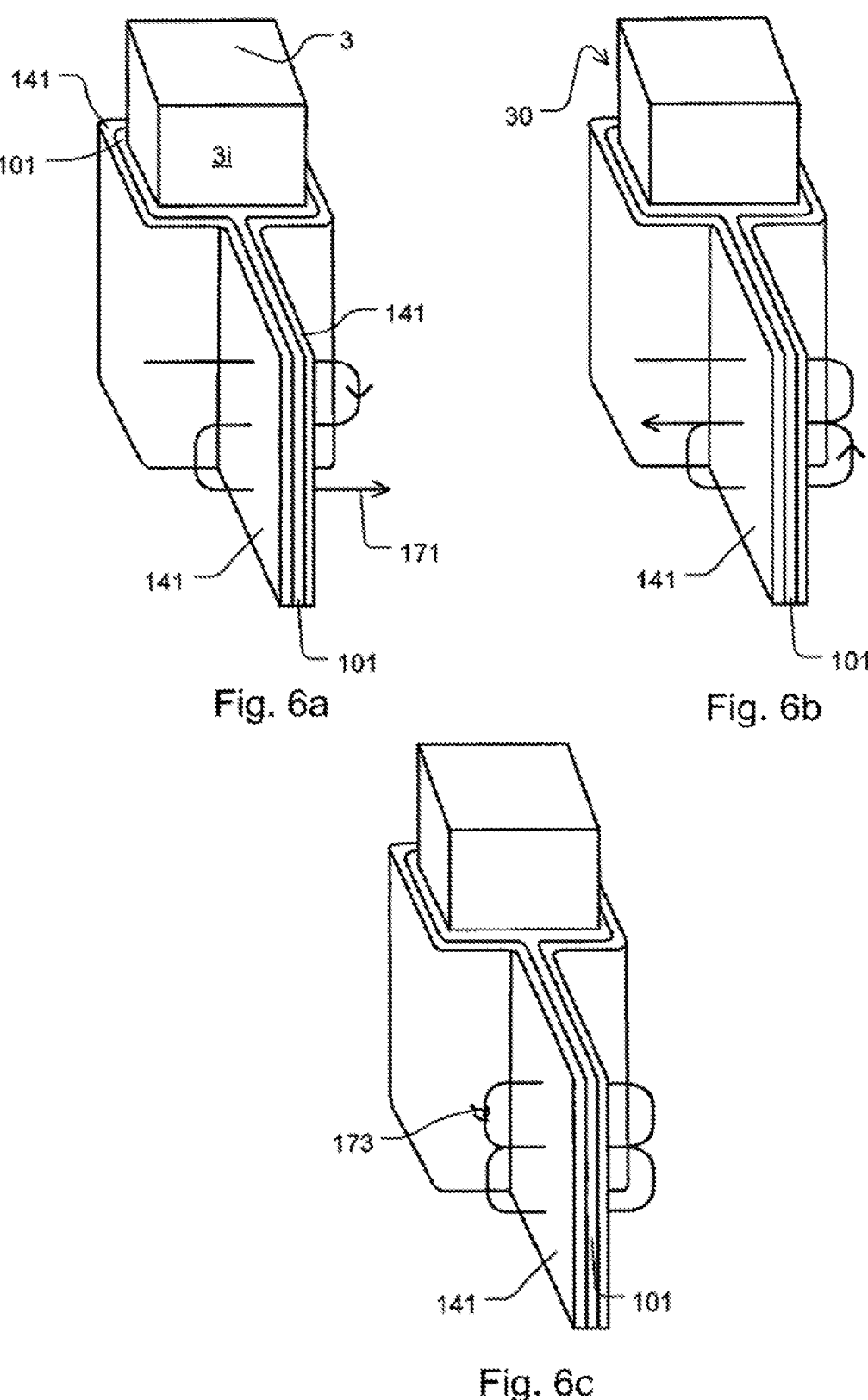
FIGS. 6a-6c show how a pledge is used for reinforcing the connection of the heart valve according to the frame of the present invention.

FIGS. 6a to 6c show how one of optional pledges 141, 141', 141" as described above is used for reinforcing the connection of the heart valve 100 to the frame 1.

FIGS. 6a to 6c show a post 3 having an outside face 3o and an inside face 3i. Outside face 3o is directed to an outside of frame 1 whereas inside face 3i is directed to an inside of frame 1.

A section of post 3 which is enwrapped by a leaflet 101 is now also enwrapped by a pledge 141 such that the free ends of pledge 141 are put above each other or superposed (only separated from each other by the leaflet 101 arranged between the free ends of the pledge 141) in a inner space of frame 1, i. e. at the inside face 3i of post 3.

Starting from the top of pledge 141, a running stitch 171 is run down to the bottom of the pledge (see FIG. 6a) and then back up to the top (see FIG. 6b). A knot 173 is made using the beginning suture's tail (see FIG. 6c). Preferably, the knot 173 is on the side of the pledge 141 and does not contact the leaflet 101.

Figure 7A:
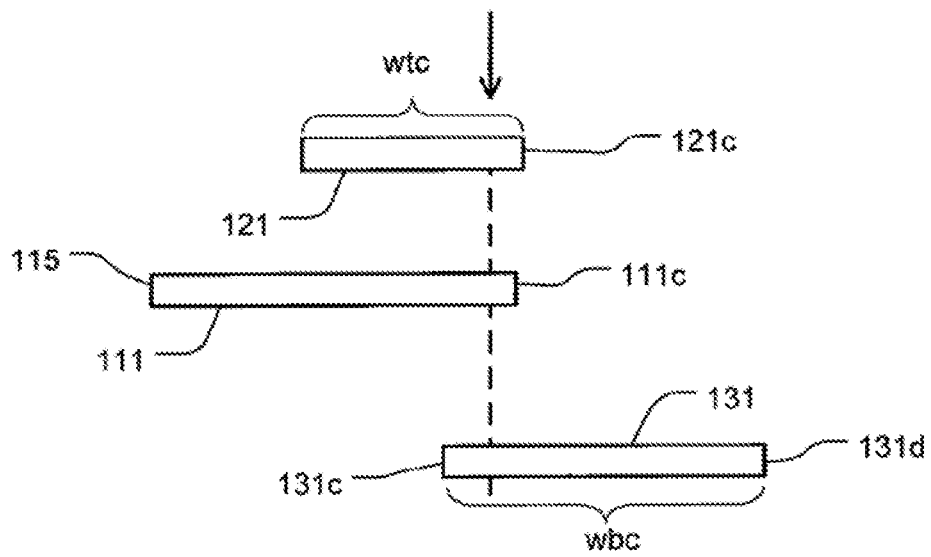
FIGS. 7a-7b show a top cuff and a bottom cuff sewed to the crown piece.

FIGS. 7a shows the top cuff 121 and the bottom cuff 131 before being interconnected, e. g. sewed, to the crown piece 111, in an exploded view.

If sewed, the arrow indicates the direction of how a first stitch of a suture 211 (see FIG. 7b) may be made.

As can be seen from FIG. 7a, the crown piece 111 may be posed between the top cuff 121 and the bottom cuff 131.

Also, the three elements 111, 121, 131 may be interconnected such that an end of the inner rim or side 121c of the top cuff 121 and an end of the lower rim or side 111c of the crown piece 111 are aligned at one side (see the right hand side in FIG. 7a) such that they end on a common level, whereas an end of the inner rim or side 131c of the bottom cuff 131, which extends remarkably beyond the ends of inner rim 121c and lower side 111c to the right in FIG. 7a, is not aligned with the ends of the lower rim or side 111c and the inner side 121c.

Figure 7B:
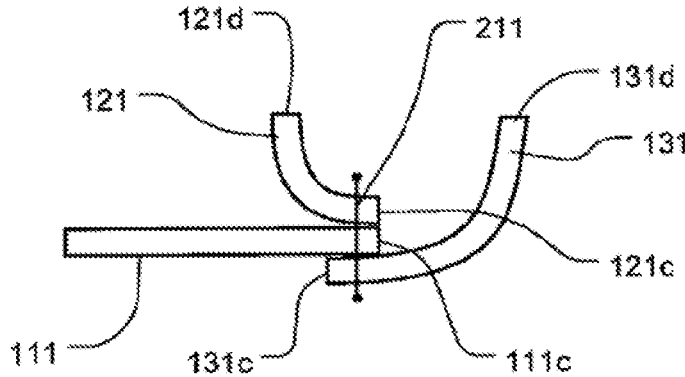

FIG. 7b shows the elements of FIG. 7a interconnected with each other, here by means of an exemplary suture, denoted by reference numeral 211. As mentioned above with respect to certain exemplary embodiments according to the present invention suture 211 may run along the entire length 1 (see FIGS. 1b to 1d). Suture 211 may be the sole or only suture used for interconnecting these three elements.

Both the top cuff 121 and the bottom cuff 131 are bend upwards (with regards to FIG. 7b) to assume a c-shape which is open towards the top of FIG. 7b. The c-shape is very similar to the shape bars 11 assume in FIG. 2. Hence, the c-shape is well-suited if the combination of top cuff 121 and bottom cuff 131 is to cover bars 11 in practice from in inner side of the guiding structure 2a, 2b shown in FIG. 2.

The expansion of frame 1 may benefit or result from, in the present exemplary embodiment, from the internal stress or from shape-memory capacities of frame 1. The frame 1 may be manufactured from Nitinol or comprise such material.

REFERENCE NUMERALS 1 frame
2a first or upper guiding structure 2b second or lower guiding structure 2b' top portion of the bars
2b" bottom portion of the bars
3 posts
3i inside face of post 3
3o outside face of post 3
5 reins or tension thread(s)
6 catheter
8 through opening (s) or, as in particular embodiments; eyelet (s)
9 connecting sections
10 apertures
11 bars
100 heart valve
101, 101', 101" leaflets
103 body of the heart valve 100
103a curved bottom section
103b rim section of the body of the leaflet
103c, 103d opposing tabs
111 crown piece
111a, 111b free end
111c lower rim or side of the crown piece
111e end of the lower rim or side of the crown piece
113, 113', 113" small tabs
115, 115' 115" round portions
121 top cuff
121a, 121b ends of top cuff
121c inner rim or side of top cuff
121d outer rim or side of top cuff
121e end of the inner rim or side of top cuff
131 bottom cuff
131a, 1316b ends of bottom cuff
131c inner rim or side of bottom cuff
131d outer rim or side of bottom cuff
131e end of the inner rim or side of bottom cuff
141, 141', 141" pledges
161 knot
163 suture tail
165 running stitch or suture
167 knot

173 knot
201 suture between crown piece and through hole
203 knot
211 suture interconnecting both the top cuff and the bottom cuff to the crown piece
l length of the stripe
rtc radius
rbc radius
wtc width of top cuff
wbc width of bottom cuff cm 1-16. (canceled)
What is claimed is:

1. A foldable and/or unfoldable medical implant comprising a heart valve (100) and a foldable and/or unfoldable frame (1) being interconnected to the heart valve (100), by sewing or sewing alone, the frame (1) comprising:
   a first ring structure (2a),
   a second ring structure (2b),
   at least one first tension thread (5) guided by the first ring structure (2a) for folding and/or unfolding the frame (1) around or along the frame (1) at an outside or an outer circumference thereof;
   at least one second tension thread (5) guided by the second ring structure (2b) for folding and/or unfolding the frame (1) around or along the frame (1) at an outside or an outer circumference thereof;
   posts (3), the posts (3) being arranged between the first and the second ring structures (2a, 2b) in order to interconnect the first and the second ring structures (2a, 2b) with each other and/or to maintain a distance between the first and the second ring structures (2a, 2b);
   and the heart valve (100), comprising:
      a ring-shaped crown piece (111), the ring-shaped crown piece (111) having opposing first and second axial ends, the first axial end of the ring-shaped crown piece having a plurality of connecting rims that are arranged one after another along a circumferential direction of the ring-shaped crown piece (111);
      leaflets (101, 101', 101") connected to the first axial end of the ring-shaped crown piece (111) at the plurality of connecting rims respectively, each of the leaflets (101, 101', 101") having a fixed first end connected to a respective one of the plurality of connecting rims of the ring-shaped crown piece (111) and a free second end opposite to the fixed first end;
      a ring-shaped top cuff (121); and
      a ring-shaped bottom cuff (131), wherein the ring-shaped crown piece (111), the ring-shaped top cuff (121) and the ring-shaped bottom cuff (131) are separate pieces, with each of the ring-shaped top cuff (121) and the ring-shaped bottom cuff (131) being interconnected with the second axial end of the ring-shaped crown piece (111), and the ring-shaped top cuff (121) and the ring-shaped bottom cuff (131) covering a same radial side of the frame (1),
   wherein the ring-shaped crown piece (111) has a plurality of connecting portions that are arranged corresponding to and sewed to the posts (3).

2. The medical implant according to claim 1, wherein at least one of the ring-shaped top cuff (121) and the ring-shaped bottom cuff (131) is formed from or comprises a stripe, wherein the stripe is curved along its length.

3. The medical implant according to claim 1, wherein the ring-shaped top cuff (121) has a width (wtc) that is smaller than a width (wbc) of the ring-shaped bottom cuff (131).

4. The medical implant according to claim 1, wherein all of the leaflets (101, 101', 101") are sewed to the ring-shaped crown piece (111) by means of one common suture or one suture each.

5. The medical implant according to claim 1, wherein both the ring-shaped top cuff (121) and the ring-shaped bottom cuff (131) are sewed to the ring-shaped crown piece (111) by one suture.

6. The medical implant according to claim 1, wherein the ring-shaped crown piece (111) or a section thereof is interposed between the ring-shaped top cuff (121) and the ring-shaped bottom cuff (131).

7. The medical implant according to claim 1, wherein the ring-shaped crown piece (111) is sewed to the posts (3) via through holes (8) of the posts (3) by one suture (201).

8. The medical implant according to claim 7, wherein the suture (201) was started from an outer side (30) of the posts (3) to an inner side (3i) of the posts (3), such that an only knot (203) that interconnects both ends of the suture (201) is arranged on the outer side (30) of the posts (3).

9. The medical implant according to claim 1, wherein the posts (3) are arranged inside a circle or an area circumscribed by the ring-shaped crown piece (111).

10. The medical implant according to claim 1, wherein the posts (3) are arranged outside a circle or an area circumscribed by at least one of the ring-shaped top cuff (121) and the ring-shaped bottom cuff (131).

11. The medical implant according to claim 1, wherein each of the first and the second ring structures (2a, 2b) comprises or consists of bars (11) that are interconnected to each other, so as to form a zig-zag pattern or an undulating or meandering pattern, and wherein the bars (11) are arranged outside a circle or an area circumscribed by at least one of the ring-shaped top cuff (121) and the ring-shaped bottom cuff (131).

12. The medical implant according to claim 1, wherein each of the leaflets (101, 101', 101") has a first tab (103c, 103c', 103c") and a second tab (103d, 103d', 103d") arranged at opposite ends, and wherein tabs (103c, 103c', 103c", 103d, 103d', 103d") are sewed onto the posts (3) of the frame (1).

13. The medical implant according to claim 1, wherein two neighboring tabs (103c, 103c', 103c", 103d, 103d', 103d") of two adjacent leaflets (101, 101', 101") are sewed to a same one of the posts (3) in an overlapping manner.

14. The medical implant according to claim 13, wherein the two neighboring tabs includes a first neighboring tab and a second neighboring tab, wherein the first neighboring tab (103d') is sewed onto the same post (3) first, and wherein the second neighboring tab (103c) is sewed onto both the first neighboring tab (103d') and the same post (3) with one suture (165).

15. The medical implant according to claim 1, wherein peripheries of the frame (1), the ring-shaped crown piece (111), the ring-shaped top cuff (121) and the ring-shaped bottom cuff (131) conform one another in the circumferential direction of the ring-shaped crown piece (111).

16. The medical implant according to claim 1, wherein the ring-shaped top cuff (121) and the ring-shaped bottom cuff (131) are partially offset in an axial direction of the frame (1).

* * * * *